(12) United States Patent
Altman et al.

(10) Patent No.: US 7,340,030 B2
(45) Date of Patent: Mar. 4, 2008

(54) ASYMMETRIC CONE BEAM

(75) Inventors: Amiaz Altman, Tel Aviv (IL); Ehud Dafni, Caesaria (IL); Armin Marcovitch, Kiryat Motzkin (IL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/546,016

(22) PCT Filed: Feb. 20, 2003

(86) PCT No.: PCT/IL03/00138

§ 371 (c)(1),
(2), (4) Date: Aug. 18, 2005

(87) PCT Pub. No.: WO2004/075118

PCT Pub. Date: Sep. 2, 2004

(65) Prior Publication Data

US 2006/0159222 A1 Jul. 20, 2006

(51) Int. Cl.
*G01N 23/083* (2006.01)
*G01T 1/16* (2006.01)
*H01L 27/146* (2006.01)

(52) U.S. Cl. .................... 378/19; 250/370.09
(58) Field of Classification Search ......... 378/4–20, 378/62, 145–153, 205, 210; 250/370.09
See application file for complete search history.

(56) References Cited

U.S. PATENT DOCUMENTS

| | | | |
|---|---|---|---|
| 4,709,382 A * | 11/1987 | Sones | 378/62 |
| 5,001,347 A * | 3/1991 | Hsieh | 250/363.1 |
| 5,187,659 A * | 2/1993 | Eberhard et al. | 378/9 |
| 5,625,661 A | 4/1997 | Oikawa | |
| 6,157,696 A * | 12/2000 | Saito et al. | 378/19 |
| 6,215,843 B1 * | 4/2001 | Saito et al. | 378/19 |
| 6,327,329 B1 | 12/2001 | Bromberg et al. | |
| 6,735,271 B1 * | 5/2004 | Rand et al. | 378/4 |
| 7,020,243 B2 * | 3/2006 | Hsieh | 378/62 |

(Continued)

FOREIGN PATENT DOCUMENTS

EP 0 182 529 A2 5/1986

(Continued)

OTHER PUBLICATIONS

Cao, Z.J., et al.; Improved Image Quality for Asymmetric Double-focal Cone-beam SPECT; 1993; IEEE Trans. on Nuc. Sci.; 40(4):1145-1148.

(Continued)

*Primary Examiner*—Edward J. Glick
*Assistant Examiner*—Anastasia S. Midkiff

(57) ABSTRACT

A multislice CT scanner for imaging a patient comprising: an X-ray source that generates a cone beam of X-rays radiated from a focal spot of the X-ray source wherein the X-ray source is moveable in a rotation plane so as to rotate the focal spot about an axial direction along which the patient is moved to position the patient in a field of view of the scanner; and a detector array comprising a plurality of rows of X-ray detectors that generate signals responsive to X-rays in the cone beam, which signals are used to generate an image of the patient; wherein the cone beam is asymmetric with respect to the rotation plane.

19 Claims, 6 Drawing Sheets

U.S. PATENT DOCUMENTS

| | | |
|---|---|---|
| 7,027,552 B2 * | 4/2006 | Shechter .................... 378/4 |
| 2001/0028697 A1 * | 10/2001 | Nahaliel et al. .............. 378/19 |
| 2002/0054659 A1 * | 5/2002 | Okumura et al. ............. 378/19 |
| 2003/0043958 A1 * | 3/2003 | Mihara et al. ................ 378/4 |
| 2004/0017888 A1 * | 1/2004 | Seppi et al. ................... 378/57 |
| 2004/0057554 A1 * | 3/2004 | Bjorkholm ................. 378/143 |
| 2004/0109532 A1 * | 6/2004 | Ford et al. .................... 378/57 |
| 2004/0165695 A1 * | 8/2004 | Karimi et al. ................ 378/19 |
| 2004/0208278 A1 * | 10/2004 | Hagiwara et al. ............. 378/16 |
| 2005/0058254 A1 * | 3/2005 | Toth et al. .................. 378/156 |
| 2005/0063514 A1 * | 3/2005 | Price et al. .................. 378/119 |

FOREIGN PATENT DOCUMENTS

EP      1 096 426 A1      5/2001

OTHER PUBLICATIONS

Zheng, G.L., et al.; Cone-Beam Iterative Reconstruction of a Segment of a Long Object; 2002: IEEE Trans. on Nuc. Sci.; 49(1): 37-41.

Zheng, G. L., et al.: Asymmetric Cone-Beam Transmission Tomography; 2001; IEEE Trans. on Nuc. Sci.; 48(1): 117-124.

* cited by examiner

ASYMMETRIC CONE BEAM

FIELD OF THE INVENTION

The present invention relates to computerized tomography (CT) X-ray imaging, and in particular to a size and shape of X-ray cone beams and corresponding X-ray detector arrays in multislice CT scanners.

BACKGROUND OF THE INVENTION

In CT X-ray imaging of a patient, X-rays are used to image internal structure and features of a region of interest (ROI) of the patient's body. A multislice CT scanner generally comprises an X-ray source that provides a cone shaped X-ray beam radiated from a focal spot of the X-ray source and an X-ray detector array comprising a plurality of closely spaced rows of X-ray detectors that face the X-ray source. In third generation multislice scanners both the X-ray source and detector array are mounted in a rotor of a gantry. In fourth generation multislice scanners the X-ray source is mounted to the rotor but the X-ray detector array, in which detectors comprised in the array form complete circles of detectors, is mounted to the gantry.

A patient being imaged with the scanner is generally supported on a bed which is moved axially along a z-axis to position the ROI in a field of view (FOV) of the scanner located inside the rotor, between the X-ray source and detector array. The rotor is rotatable around the z-axis so as to position the X-ray source, and in third generation CT scanners the detector array, at different cone beam view angles around the patient, from which view angles the X-ray source illuminates the ROI with X-rays. Measurements of intensity of X-rays from the X-ray source that pass through the patient's body at the different view angles provide measurements of attenuation of the X-rays for different attenuation paths through the body. The attenuation measurements are used to image the ROI.

As the rotor is rotated, motion of the X-ray source focal spot occurs in a plane, hereinafter referred to as a "rotation plane", generally perpendicular to the z-axis. A vertex angle of a fan shaped cross section of the cone beam in the rotation plane is a "fan angle" of the cone beam. A vertex angle of a fan-shaped cross section of the cone beam in a plane perpendicular to the rotation plane that passes through the focal spot and the z-axis is a "cone beam angle" of the cone beam. The cone beam is substantially symmetric relative to the rotation plane and the rotation plane bisects the cone beam angle of the cone beam. To match the symmetric cone beam, the rows of the X-ray detectors in the detector array are symmetrically disposed relative to the rotation plane i.e. each row has a mirror image row in the rotation plane.

For a given size fan angle, the cone beam volume and size of the detector array, and for a given size of X-ray detectors in the detector array, the number of detector rows in the array, are limited by the cone beam angle. The cone beam angle in turn is limited inter alia by an effect referred to as a heel effect.

Let an angle relative to the rotation plane of a path along which X-rays radiated from the X-ray source focal spot propagate be referred to as "declination angle". It is convenient to define declination angles to be positive on one side, a positive side, of the rotation plane and to be negative on the other side, a negative side, of the rotation plane. The heel effect hardens and decreases intensity of X-rays emanating from the X-ray source as the magnitude of the declination angle increases on one side, arbitrarily the negative side, of the rotation plane. The hardening and intensity reduction is a result of a configuration of an anode comprised in the X-ray source onto which an electron beam is focussed to generate X-rays. As a result of the configuration, for increasingly negative declination angles, as X-rays generated in the anode leave the target, they encounter on the average a greater amount of material from which the anode is formed. As the amount of anode material that the X-rays traverse increases, attenuation and hardening of the X-rays increase, generating thereby the heel effect.

The hardening and drop in intensity as a function of decreasing declination angle determines a minimum declination angle, hereinafter a "heel effect angle" for X-rays below which intensities and energies of X-rays are generally not effective for CT imaging. As a result of the symmetry of the cone beam relative to the rotation plane, a maximum positive declination angle for X-rays is equal to the magnitude of the heel effect angle. The cone beam therefore has a cone beam angle equal to about twice the magnitude of the heel effect angle. The heel effect therefore limits the cone beam angle, and thereby a volume of the cone beam, a total number (for a given detector size) of detector rows in the scanner and a volume of a patient for which CT scan data can be simultaneously acquired.

In order to provide faster CT imaging of patients and enable imaging of moving organs of the body with improved temporal resolution, for example cardiac imaging, there is a need to increase the volume of a patient for which data is simultaneously acquired by a multislice scanner.

SUMMARY OF THE INVENTION

An aspect of some embodiments of the present invention relates to providing a multislice CT scanner having a cone beam for which the cone beam angle and thereby cone beam volume are larger than cone beam angles and volumes of prior art cone beams having a same fan angle.

The inventors have noted that the heel effect does not substantially affect intensity and hardness of X-rays on the positive side of a CT scanner rotation plane and that X-rays having declination angles greater than the magnitude of the heel effect angle have intensities and energies useful for CT imaging. However, X-rays having declination angles greater than the magnitude of the heel effect angle are not used in prior art scanners as a result of the prior art constraint that a CT cone beam be symmetric with respect to its rotation plane.

Therefore, a cone beam of a CT scanner in accordance with some embodiments of the invention is not symmetric with respect to its rotation plane but is larger on the positive side of the rotation plane than on the negative side. As a result, the cone beam angle and volume of the cone beam is not limited by its heel effect angle and are larger than a cone beam angle and (for a same fan angle) a volume of a corresponding prior art cone beam having a same heel effect angle. A matching detector array, in accordance with the present invention, is also asymmetric with respect to the rotation plane and for a same fan angle, larger than a prior art detector array. A CT scanner comprising a cone beam in accordance with the invention can therefore generally simultaneously acquire data for a larger volume of a patient than a CT scanner comprising a corresponding prior art cone beam.

According to an aspect of some embodiments of the invention, on the positive side of the rotation plane, a number of X-ray detector rows in the matching detector array is greater than a number of detector rows on the negative side of the rotation plane.

According to an aspect of some embodiments of the invention a width of at least one detector row on the positive side of the rotation plane is different from widths of detector rows on the negative side of the rotation plane.

According to an aspect of some embodiments of the invention, widths of detector rows increases as declination angles at which the rows are located increases.

In some embodiments of the present invention, row width of each detector row in at least a portion of the rows in the detector array is substantially proportional or equal to an apparent size of the X-ray source focal spot along the z-axis as seen from the row. Apparent z-axis size of the focal spot of the X-ray source increases with increasing declination angle of a location of the row. A detector array for a cone beam having a given cone beam angle can generally be produced with a smaller number of X-ray detectors without substantially compromising spatial resolution of the array if row widths are substantially proportional or equal to apparent focal spot size. The smaller number of X-ray detectors generally results in a lower production cost for the array.

There is therefore provide in accordance with an embodiment of the present invention, a multislice CT scanner for imaging a patient comprising: an X-ray source that generates a cone beam of X-rays radiated from a focal spot of the X-ray source wherein the X-ray source is moveable in a rotation plane so as to rotate the focal spot about an axial direction along which the patient is moved to position the patient in a field of view of the scanner, and a detector array comprising a plurality of rows of X-ray detectors that generate signals responsive to X-rays in the cone beam, which signals are used to generate an image of the patient; wherein the cone beam is asymmetric with respect to the rotation plane.

Optionally, trajectories of X-rays on a first side of the rotation plane that are incident on the detector array have declination angles relative to the rotation plane that have a first maximum magnitude and trajectories of X-rays incident on the detector array on a second side of the rotation plane have declination angles that have a second maximum magnitude greater than the first maximum.

Optionally, the second maximum magnitude is greater than 1.25 times the first maximum magnitude. Alternatively, the second maximum magnitude is optionally greater than 1.5 times the first maximum magnitude. Alternatively, the second maximum magnitude is optionally greater than twice the first maximum magnitude.

In some embodiments of the present invention, the first maximum angle is determined substantially by the heel effect.

In some embodiments of the present invention, the detector rows are substantially parallel to the rotation plane and a width of each row in at least a portion of the rows is a function of a declination angle relative to the rotation plane of a line from the focal spot to the row.

There is further provided in accordance with an embodiment of the present invention a multislice CT scanner for imaging a patient comprising: an X-ray source that generates a cone beam of X-rays radiated from a focal spot of the X-ray source wherein the X-ray source is moveable in a rotation plane so as to rotate the focal spot about an axial direction along which the patient is moved to position the patient in a field of view of the scanner; and a detector array comprising a plurality of rows of X-ray detectors that generate signals responsive to X-rays that are used to generate an image of the patient; wherein the detector rows are substantially parallel to the rotation plane and a width of each row in at least a portion of the rows is a function of a declination angle relative to the rotation plane of a line from the focal spot to the row.

Additionally or alternatively, the declination angle of a row optionally increases in a direction from the first side to the second side and the width of each row in the at least portion of the rows increases as its declination angle increases.

Optionally, the focal spot is tilted with respect to the rotation plane at an angle $\beta$ and the width of each row in the at least portion of the rows is substantially proportional to $1/\sin(\beta+\phi)$ where $\phi$ is the declination angle of the row.

Optionally, the width of each row in the at least portion of the rows is substantially equal to $1/L\sin(\beta+\phi)$ where L is a dimension of the focal spot along the direction along which the focal spot is tilted.

BRIEF DESCRIPTION OF FIGURES

Non-limiting examples of embodiments of the present invention are described below with reference to figures attached hereto and listed below. In the figures, identical structures, elements or parts that appear in more than one figure are generally labeled with a same numeral in all the figures in which they appear. Dimensions of components and features shown in the figures are chosen for convenience and clarity of presentation and are not necessarily shown to scale.

DETAILED DESCRIPTION OF EXEMPLARY EMBODIMENTS

Figure 1:
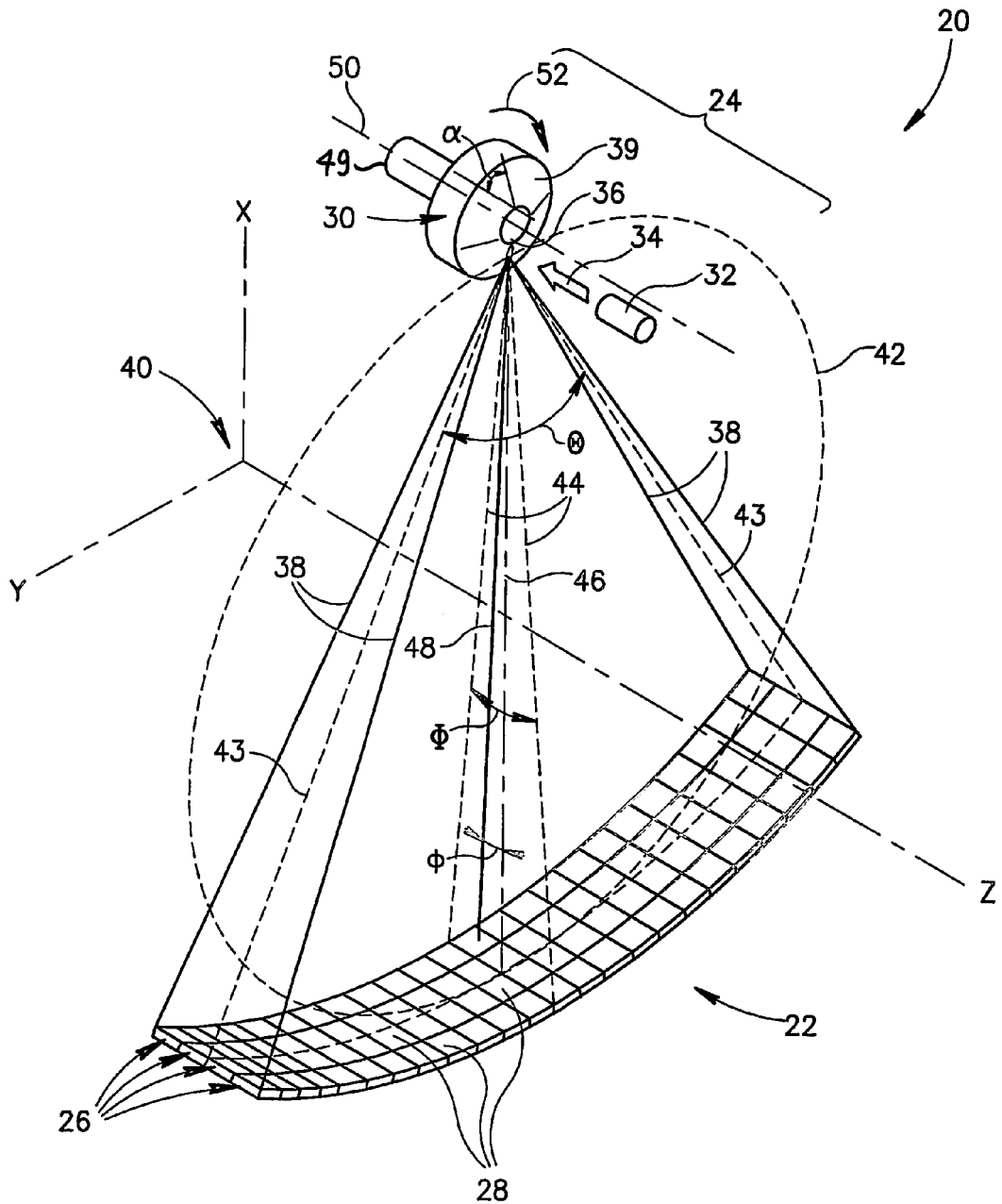
FIG. 1 schematically shows a perspective view of a multislice CT scanner comprising an X-ray cone beam and detector array, in accordance with prior art.

FIG. 1 schematically shows a perspective view of a third generation multislice CT scanner 20 comprising an X-ray detector array 22 and an X-ray source 24 in accordance with prior art. Only features of multislice scanner 20 germane to the present discussion are shown in FIG. 1.

X-ray detector array 22 comprises a plurality of rows 26 of X-ray detectors 28. By way of example, in FIG. 1 detector array 22 is shown comprising four detector rows 28. X-ray source 24 comprises an anode 30, formed with or mounted on a shaft 49, and a cathode 32. The cathode provides a beam of electrons represented by a block arrow 34, which is focussed to a "focal spot" 36 on a surface 39 of the anode. Bremmstrahlung and fluorescent X-rays generated by electrons in the beam that are incident on anode 30 are radiated from material in a neighborhood of focal spot 36 in an X-ray cone beam outlined by lines 38. The cone beam will hereinafter be referred to by the numeral 38 labeling the lines that outline the cone beam. X-rays in cone beam 38 illuminate X-ray detector array 22. At least one collimator (not shown) comprised in X-ray source 24 collimates X-rays radiated from focal spot 36 so that cone beam 38 illuminates substantially all of and only detector array 22.

X-ray source 24 and detector array 22 are mounted to a rotor (not shown) comprised in the scanner. The rotor is rotatable around a z-axis of a coordinate system 40 so as to position X-ray source 24 and detector array 22 at different cone beam view angles about the z-axis. Motion of focal spot 36 during rotation of the rotor defines a rotation plane indicated by a dashed circle 42 of CT scanner 20. Dashed lines 43 indicate a cross section of cone beam 38 in rotation plane 42. A vertex angle $\Theta$ of cross section 43 is a fan angle of cone beam 38. Dashed lines 44 indicate a cross section of cone beam 38 in a plane that passes through the z-axis and is perpendicular to rotation plane 42. A vertex angle $\Phi$ of cross section 44 is a cone angle of cone beam 38. An intersection line 46 of rotation plane 42 and the plane of cross section 44 is an axis of cone beam 38.

Cone beam 38 is symmetric with respect to rotation plane 42, the rotation plane bisects cone beam angle $\Phi$ and a same number of detector rows 26 lie on both sides of the rotation plane. A declination angle of an X-ray radiated from focal spot 36 is an angle that a propagation path of the X-ray makes with rotation plane 42. Declination angles are negative on the side of rotation plane 42 facing the origin of coordinate system 40 and positive on the other side. An X-ray propagation path 48 having a negative declination angle $\phi$ is shown in FIG. 1.

X-ray source 24 is typically operated at power levels sufficiently high so that local heating of material in anode 30 by electron beam 34 would rapidly damage the anode. To reduce anode wear, the anode is rotated about an axis 50 and electron beam 34 is displaced along a radial direction relative to axis 50 so that focal spot 36 is not always located on a same region of surface 39. In addition, focal spot 36 is elongated along the radial direction to disperse energy deposition radially. In FIG. 1 rotation of anode 30 is indicated by curved arrow 52.

To enable focal spot 36 to be "seen" by detector array 22 and to reduce shielding of X-rays generated in anode 30 that propagate towards detector array 22 by material in the anode surface 39 is a truncated conical surface having a cone angle $\alpha$. However, cone angle $\alpha$ is generally made relatively large so that an effective size of focal spot 36 as seen by detector array 22 is small enough so that the extended length of the focal spot does not impair resolution along the z-axis direction of CT scanner 20.

Figure 2:
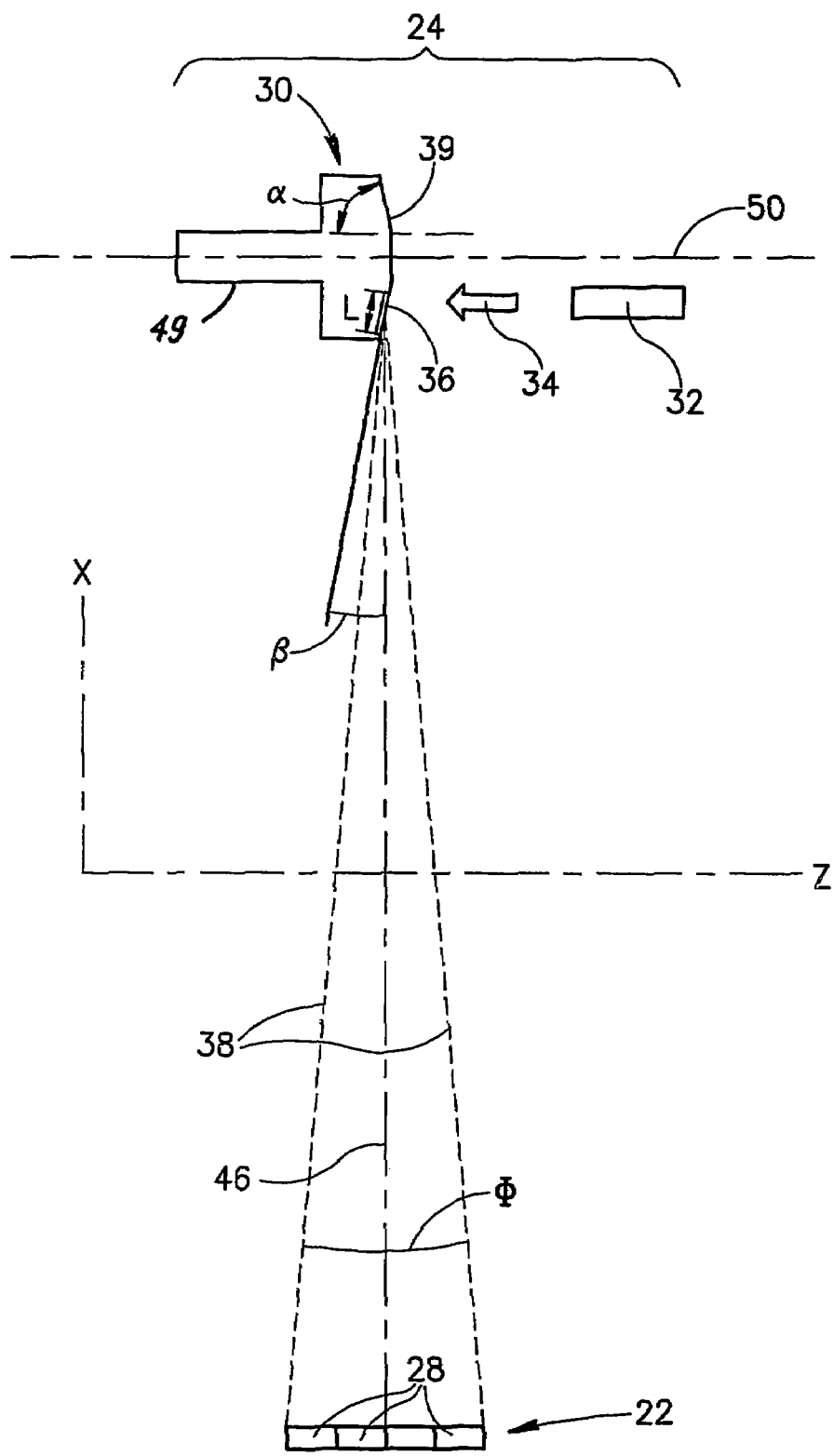
FIG. 2 schematically shows a cross section view of the multislice CT shown in FIG. 1.

Spatial relations between the geometry of conical surface 39 focal spot 36, cone beam 38 and detector array 22 are conveniently seen in FIG. 2, which schematically shows a cross section view of CT scanner 20 in the plane of cross section 44 of cone beam 38. As a result of the cone angle $\alpha$ of conical surface 39, the region of the surface on which focal spot 36 is located is tilted with respect to rotation plane 42 and has a "slope angle" $\beta=(90°-\alpha)$ with respect to the rotation plane. If L is the radial extent of focal spot 36 on surface 39 an average effective "z-axis" size, "$L_z$", of focal spot 36 parallel to the z-axis as seen by detector array 22 is substantially equal to a length of a projection of the focal spot on the detector array. $L_z$ is substantially equal to $L\sin\beta$. Ideally, focal spot 36 approaches a point source of X-rays. Therefore as L is increased to improve heat dispersion, slope angle $\beta$ is generally decreased so that $L_z$ remains sufficiently small to meet desired resolution specifications for CT scanner 20. However, as the cone surface angle $\alpha$ increases and the slope angle $\beta$ of anode 30 decreases, the heel effect angle (and as a result the cone beam angle) of cone beam 38 decreases. The heel effect angle, "$\phi_H$", is generally equal to about $(-\beta+\gamma)$ where $\gamma$ is an angle that is substantially determined by a material from which the anode is made. As a result, the cone beam angle $\Phi$, which is generally equal to about twice the heel effect angle, is equal to about $2(\beta-\gamma)$. Typically, $\alpha$ has a value between about 80° and about 83°, and slope angle $\beta$ has a corresponding value between about 10° and 7°. For Tungsten $\gamma$ is equal to about 3.5°.

Figure 3:
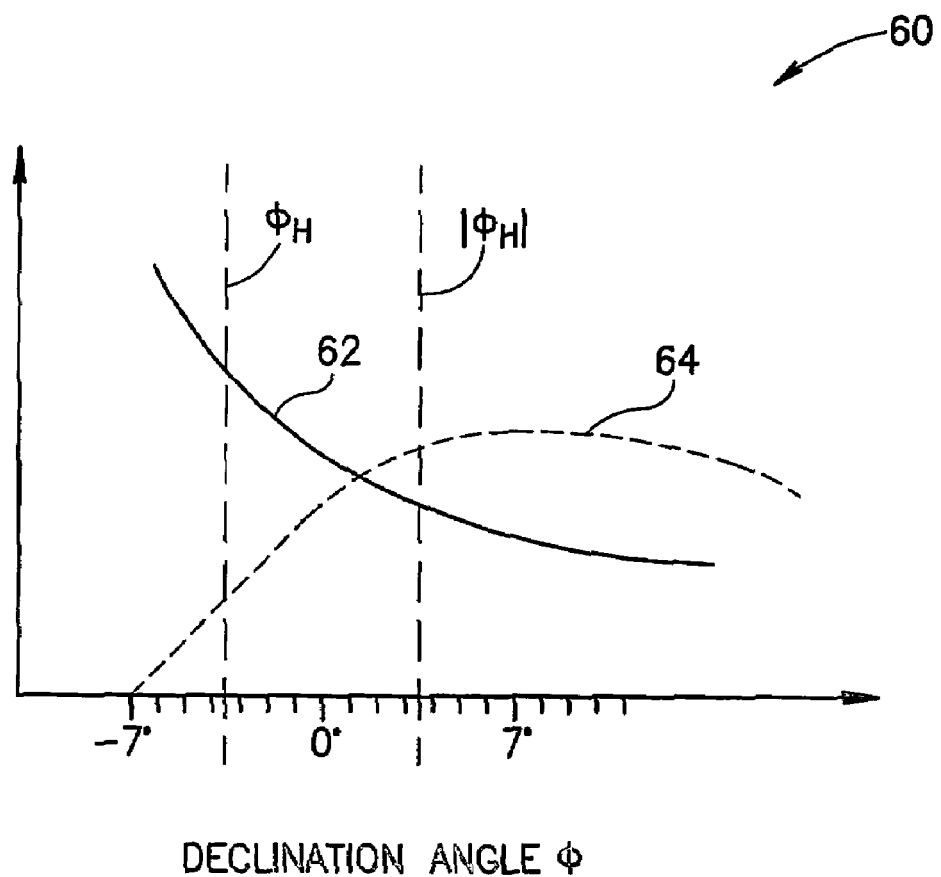
FIG. 3 shows a schematic graph illustrating decrease in intensity and hardening of X-rays in a cone beam resulting from the heel effect.

FIG. 3 shows a schematic graph 60 of intensity and mean energy of X-rays provided by X-ray source 30 shown in FIGS. 1 and 2 as a function of declination angle $\phi$ for cone surface angle $\alpha$ equal to about 83° and slope angle $\beta$ equal to about 7°. Anode 30 is assumed to be made from Tungsten so that for the anode, $\gamma=3.5°$ and X-ray source 30 has a heel effect angle, "$\phi_H$" equal to about −3.5°. Dependence of mean energy of X-rays on, declination angle is shown by a solid curve 62 and intensity is shown by a dashed curve 64. Units along the ordinate of graph 60 are arbitrary.

In general, intensity of X-rays provided by an X-ray source such as X-ray source 24 decrease relatively rapidly to zero with declination angle as the declination angle approaches $(-\beta)$. From graph 60 for example, it is seen that for slope angle $\beta=7°$, intensity of X-rays decreases rapidly for decreasing declination angle and is substantially equal to zero at a declination angle of about −7°. Mean energy of the X-rays also increases relatively rapidly as declination angle $\phi$ decreases. For declination angles $\phi$ less than or equal to the heel effect angle $\phi_H$, X-rays provided by X-ray source 24 do not have sufficient intensity and appropriate mean energy advantageous for performing CT imaging with minimal dosage to the patient. Cone beam 38 (FIGS. 1 and 2) is therefore limited to an effective minimum negative declination angle of about −3.5°. Since prior art constrains CT cone beams to be symmetric with respect to their rotation planes, cone beam 38 is limited to a maximum X-ray declination angle $\phi_+\sim|\phi_H|\sim3.5°$ and a cone beam angle equal to about 7°. The heel effect angle $\phi_H=-3.5°$ and corresponding maximum positive declination angle $\phi_+=|\phi_H|=3.5°$ which determine the cone beam angle of cone beam 38 are indicated in graph 60.

The inventors have noticed that, as shown in graph 60, whereas intensity of X-rays provided by X-ray source 24 falls off rapidly for negative declination angles, intensity remains relatively high for a substantial range of positive declination angles. In addition, rate of decrease of mean energy of the X-rays is moderated for declination angles greater than zero. It is therefore possible to provide a CT scanner having a larger cone beam and larger detector array than in prior art scanners by relaxing the prior art symmetry constraint, providing the scanner with an asymmetric cone beam and using thereby X-rays having positive declination angles greater than $|\phi_H|$. Therefore, in accordance with an embodiment of the present invention, a CT comprises an asymmetric cone beam characterized by a maximum positive declination angle $\phi+$ that is larger than the magnitude of the heel effect angle $|\phi_H|$.

It would of course also be possible to provide a CT scanner with a larger cone beam and detector array than in prior art scanners by tilting X-ray source 24 so to increase slope angle $\beta$. Whereas this would provide the scanner with a symmetric cone beam having a larger cone angle, the increased slope angle tends to reduce resolution of images provided by the scanner. The increased slope angle may also lead to undesirable loads on shaft 49 of anode 30 and bearings (not shown) that support the anode, which typically rotates at 9000 rpm.

Figure 4A:
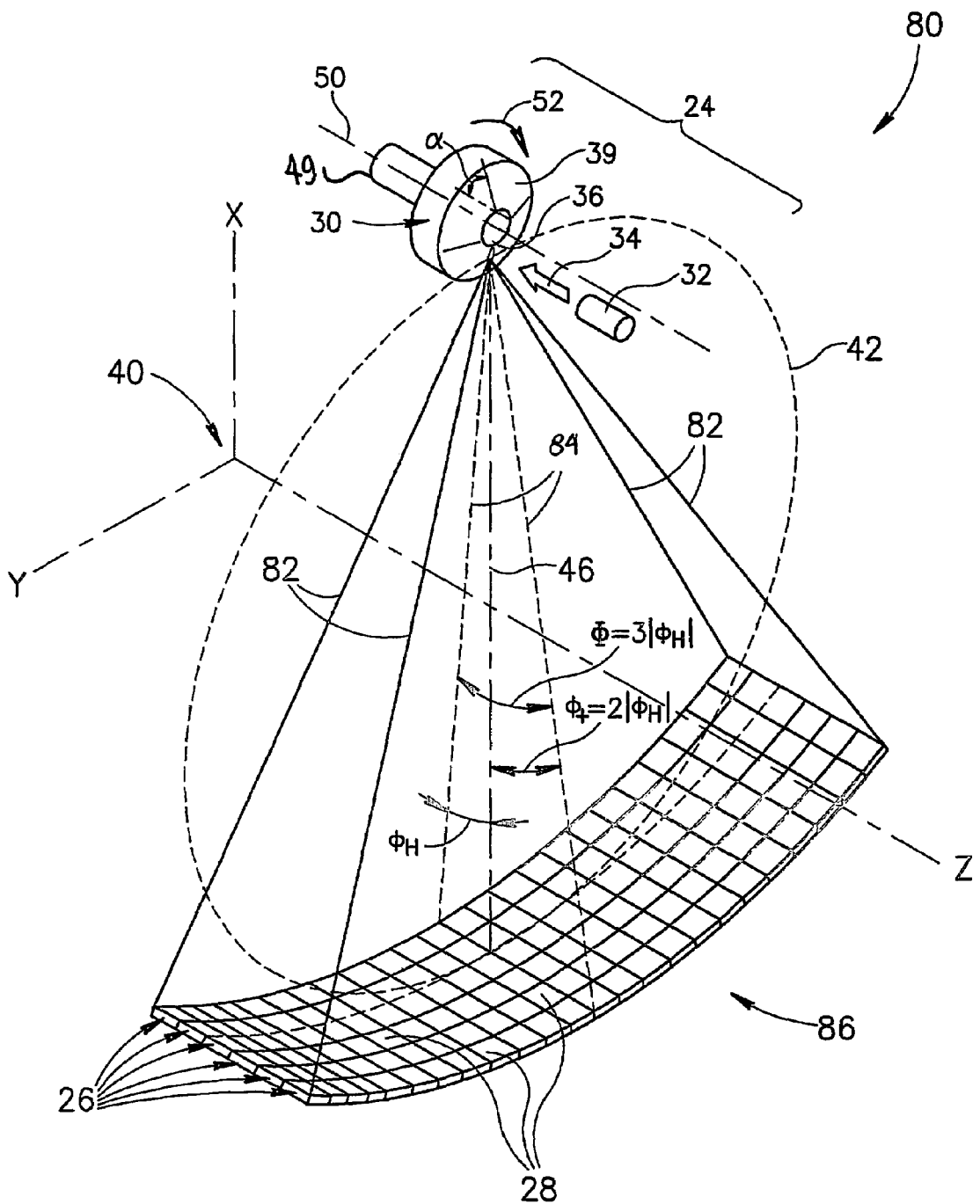
FIGS. 4A and 4B schematically show perspective and cross section views respectively of a multislice CT scanner comprising an X-ray cone beam and detector array in accordance with an embodiment of the present invention.
Figure 4B:
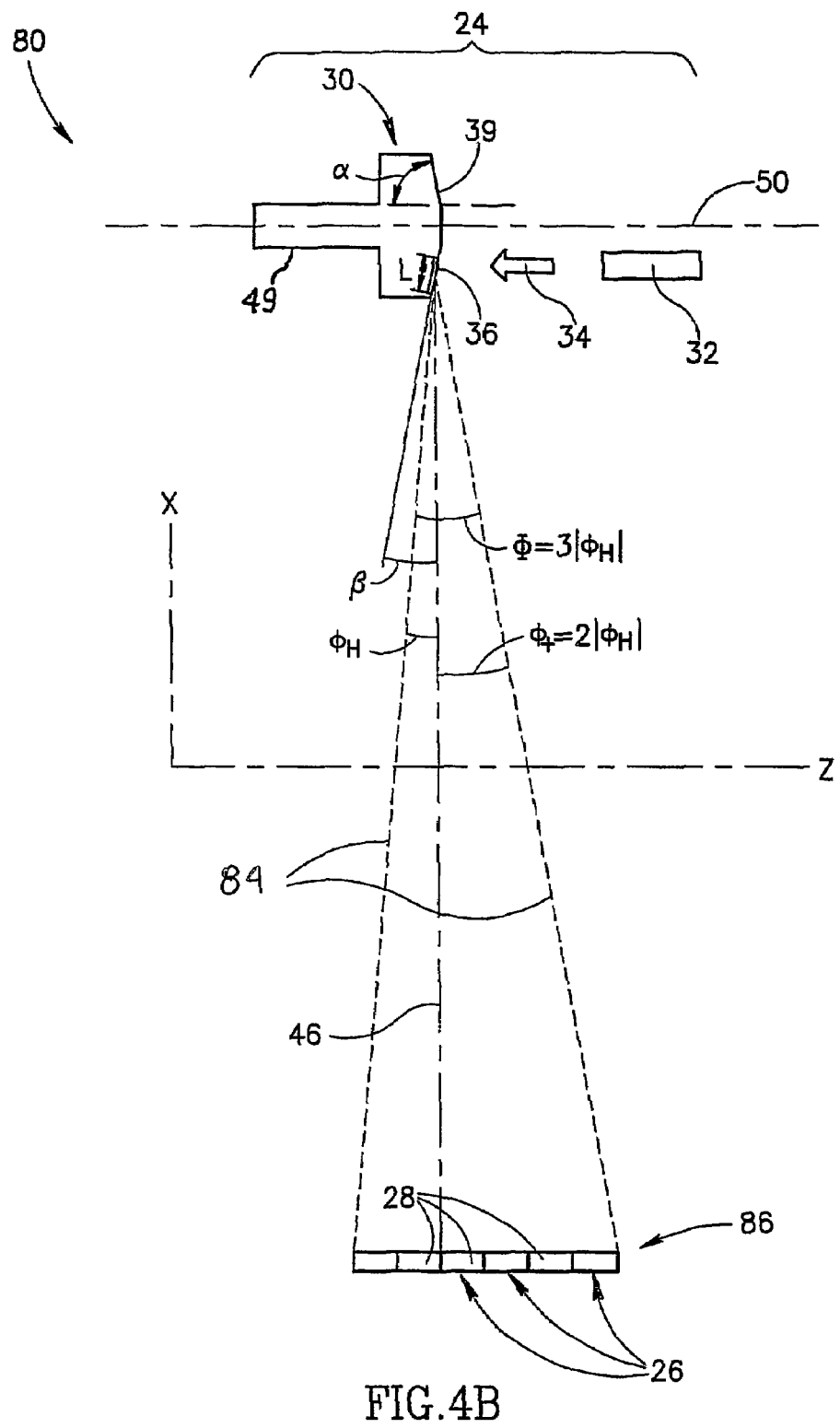

FIGS. 4A and 4B schematically show respectively a perspective view and a cross section view of a CT scanner 80 in which X-ray source 24 is collimated to provide a cone beam 82, in accordance with an embodiment of the present invention. Cone beam 82 has a cross section 84 in a plane that passes through the z-axis and is perpendicular to rotation plane 42. X-rays in cone beam 82 illuminate a matching X-ray detector array 86 comprising a plurality of rows 26 of detectors 28. Except for cone beam 82 and detector array 86, elements and features of CT scanner 80 are, by way of example, similar to corresponding elements of prior art scanner 20 (FIG. 1).

Cone beam 82 is asymmetric and optionally larger than cone beam 38 comprised in CT scanner 20. By way of example, cone beam 82 is characterized by a maximum positive declination angle $\phi+$ that is larger than the magnitude of the heel effect angle $|\phi_E|$ of X-ray source 24. As a result, cone beam 82 has a cone beam angle $\Phi=(|\phi_H|+\phi_+)$, which is greater than a typical prior art cone beam angle which is equal to about $2|\phi_H|$. In some embodiments of the present invention $\phi+$ is greater than or equal to $1.25|\phi_H|$. In some embodiments of the present invention $\phi+$ is greater than or equal to $1.5|\phi_E|$. In some embodiments of the present invention $\phi+$ is greater than or equal to $2|\phi_E|$. By way of example, for CT scanner 80, $\phi_+$ is equal to $2|\phi_E|$ and while cone beam 38 has a cone beam angle $\Phi=2|\phi_H|$, cone beam 82 has a substantially larger cone beam angle $\Phi=3|\phi_H|$.

To match asymmetric cone beam 82, detector array 86 is also asymmetric and larger than corresponding detector array 22 comprised in CT scanner 20. In some embodiments of the present invention detector array 86 comprises a larger number of detector rows 28 on the positive declination angle side of rotation plane 42 than on the negative declination angle side of the rotation plane. By way of example, CT scanner 80 is shown having two rows 28 of detectors on the negative side of rotation plane 42 and four detector rows 28 on the positive side of the rotation plane.

In some embodiments of the invention, as in FIGS. 4A and 4B, all detectors in detector array 86 have substantially a same width in the z-axis direction and all rows 28 in detector array 86 have same width. In some embodiments of the invention, detectors in at least one detector row of a CT scanner have z-axis widths larger than detectors in a different detector row of the scanner and at least two of the rows of detectors have different widths. In some embodiments of the present invention, width of a scanner detector row is a function of a declination angle $\phi$ at which the detector row is located. In some embodiments of the present invention a width of each detector row in at least a portion of the detector rows in the scanner increases as a declination angle $\phi$ at which the row is located increases.

Figure 5:
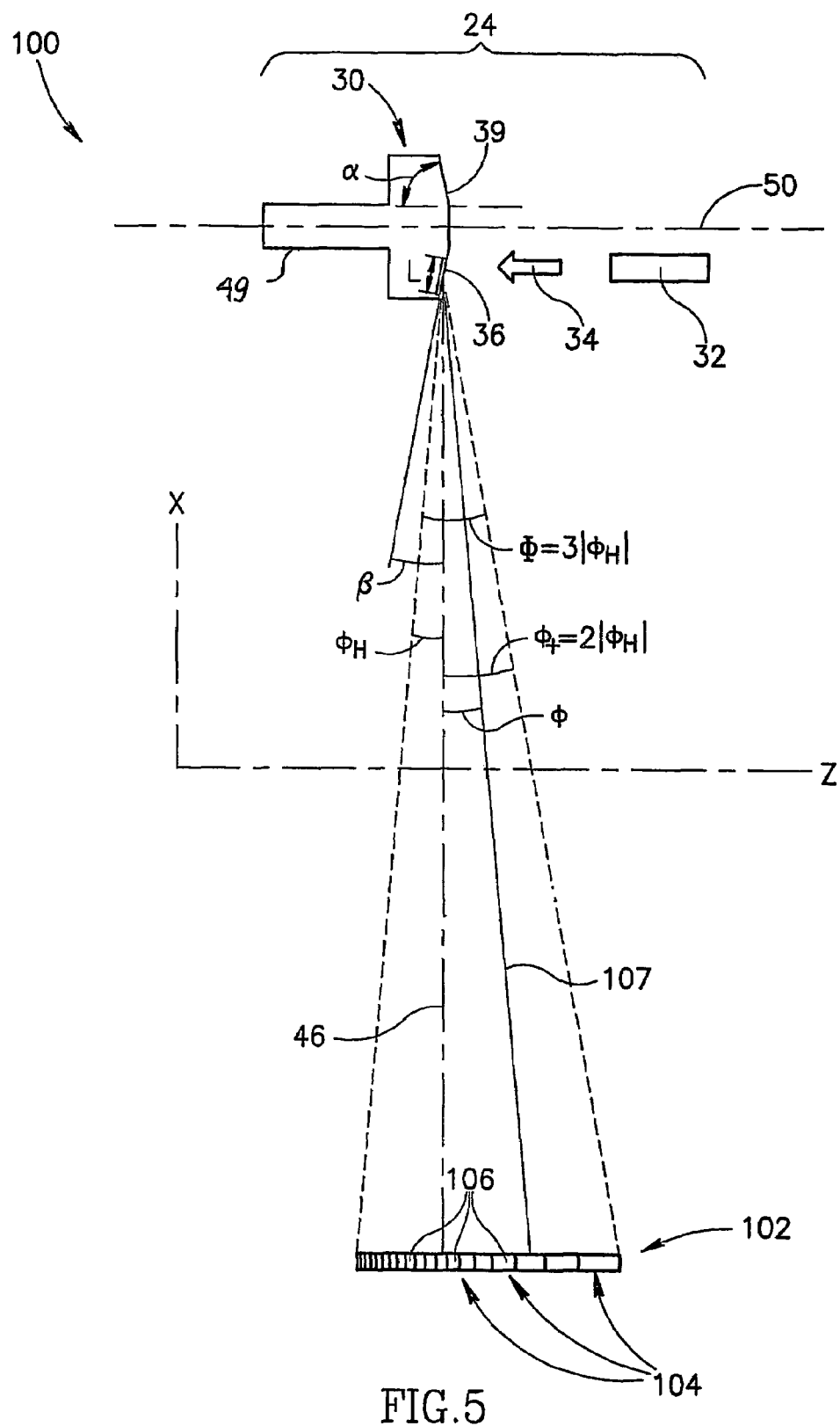
FIG. 5 schematically shows a CT scanner comprising a detector array having rows of detectors for which the widths of at least some of the rows increase as declination angles at which they are located increase, in accordance with an embodiment of the present invention.

FIG. 5 shows a schematic cross section of a CT scanner 100 comprising a detector array 102 having rows 104 of detectors 106 in which widths of rows in the array increase with increasing declination angle, in accordance with an embodiment of the present invention.

Optionally, in accordance with an embodiment of the invention, for a given radial length L and slope angle $\beta$ for focal spot 36, the width of each row in at least a portion of rows 104 is determined responsive to $L_z(\phi)=L\sin(\beta+\phi)$, where $\phi$ is the declination angle at which the row is located. By way of example, a declination angle $\phi$, is shown for a row 104 in FIG. 5. The declination angle is an angle between axis 46 and a line 107 shown intercepting a detector 106 the row.

$L_z(\phi)$ is a z-axis length of a projection of focal spot 36 on row 104 at declination angle $\phi$ and thereby an effective z-axis length of the focal spot 36 as seen by the row. In some embodiments of the invention, the widths of rows in the at least portion of rows 104 are substantially proportional to $L_z(\phi)$. In some embodiments of the invention, the widths of the rows in the at least portion of rows 104 are substantially equal to $L_z(\phi)$.

It is noted that z-axis resolution provided by a given row 104 of detectors 106 is a function of row width and generally improves as a width of the detector row decreases. However, while improvement is relatively rapid with decreasing width for widths greater than or equal to about $L_z(\phi)$ improvement is slower with decreasing width for widths less than $L_z(\phi)$. As a result, while there is incentive to reduce detector row width, for a detector row at a given declination angle $\phi$ having a corresponding $L_z(\phi)$ the incentive to reduce the row width below $L_z(\phi)$ is generally marginal.

Therefore, a detector array for a cone beam having a given cone beam angle can generally be produced with a smaller number of X-ray detectors without substantially compromising spatial resolution of the array if row widths are substantially proportional or equal to $L_z(\phi)$. The smaller number of X-ray detectors generally results in a lower production cost for the array. Cost advantages of producing X-ray detector arrays for which the row widths are proportional or equal to or $L_z(\phi)$ can be advantageous in particular for relatively large detector arrays having rows located at relatively large declination angles.

It is noted that whereas in the above discussion of detector row width in accordance with the present invention, detector array 102 is an asymmetric detector array, the discussion applies equally well to symmetric detector arrays.

In the description and claims of the present application, each of the verbs, "comprise" "include" and "have", and conjugates thereof, are used to indicate that the object or objects of the verb are not necessarily a complete listing of members, components, elements or parts of the subject or subjects of the verb.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art. The scope of the invention is limited only by the following claims.

The invention claimed is:

1. A multislice CT scanner for imaging a patient comprising:
   an X-ray source that generates a cone beam of X-rays radiated from a focal spot of the X-ray source wherein the X-ray source is moveable in a rotation plane so as to rotate the focal spot about an axial direction along which the patient is moved to position the patient in a field of view of the scanner; and
   a detector array comprising a plurality of rows of X-ray detectors that generate signals responsive to X-rays in the cone beam, which signals are used to generate an image of the patient;
   wherein the cone beam is asymmetric with respect to the rotation plane, and wherein a width of each row of X-ray detectors increases as a declination angle of a line from the focal spot to the row relative to the rotation plane increase and, wherein the width of each row is different.

2. A multislice CT scanner according to claim 1 wherein trajectories of X-rays on a first side of the rotation plane that are incident on the detector array have declination angles relative to the rotation plane that have a first maximum magnitude and trajectories of X-rays incident on the detector array on a second side of the rotation plane have declination angles that have a second maximum magnitude greater than the first maximum.

3. The multislice CT scanner according to claim 2 wherein the second maximum magnitude is greater than 1.25 times the first maximum magnitude.

4. The multislice CT scanner according to claim 2 wherein the second maximum magnitude is greater than 1.5 times the first maximum magnitude.

5. The multislice CT scanner according to claim 2 wherein the second maximum magnitude is greater than twice the first maximum magnitude.

6. The multislice CT scanner according to claim 2 wherein a first maximum angle is determined substantially by the heel effect.

7. The multislice CT scanner according to claim 1 wherein the detector rows are substantially parallel to the rotation plane.

8. A multislice CT scanner for imaging a patient comprising:
an X-ray source that generates a cone beam of X-rays radiated from a focal spot of the X-ray source wherein the X-ray source is moveable in a rotation plane so as to rotate the focal spot about an axial direction along which the patient is moved to position the patient in a field of view of the scanner; and
a detector array comprising a plurality of rows of X-ray detectors that generate signals responsive to X-rays that are used to generate an image of the patient;
wherein the detector rows are substantially parallel to the rotation plane and a width of each row in at least a portion of the rows is different from a width of the other rows and increases with an increasing declination angle relative to the rotation plane of a line from the focal spot to the row, and wherein the width of each row of X-ray detectors is inversely proportional to a sine of the declination angle.

9. The multislice CT scanner according to claim 7 wherein the declination angle of a row increases in a direction from a first side to a second side.

10. The multislice CT scanner according to claim 9 wherein the focal spot is tilted with respect to the rotation plane at an angle $\beta$ and the width of each row in the at least portion of the rows is substantially proportional to $1/\sin(\beta+\phi)$ where $\phi$ is the declination angle of the row.

11. The multislice CT scanner according to claim 10 wherein the width of each row in the at least portion of the rows is substantially equal to $1/L\sin(\beta+\phi)$ where L is a dimension of the focal spot along the direction along which the focal spot is tilted.

12. The multislice CT scanner according to claim 1 wherein the width of each row of X-ray detectors is inversely proportional to a sine of a tilt angle at which the focal spot is tilted with respect to the rotation plane.

13. The multislice CT scanner according to claim 1 wherein the width of each row of X-ray detectors is a function of $1/\sin(\beta+\phi)$, wherein $\phi$ is the declination angle of the row and $\beta$ is the tilt angle at which the focal spot is tilted with respect to the rotation plane.

14. The multislice CT scanner according to claim 1 wherein the width of each row of X-ray detectors is a function of $1/(L*\sin(\beta+\phi))$, wherein L is a dimension of the focal spot along a direction along which the focal spot is tilted, $\phi$ is the declination angle of the row, and 3 is the angle at which the focal spot is tilted with respect to the rotation plane.

15. A method, comprising:
generating a cone beam of X-rays from a focal spot of an X-ray source, wherein the X-ray source rotates about a rotation axis along an axial direction and the cone beam of X-rays traverses a field of view;
detecting the cone beam of X-rays with a multislice detector having a plurality of rows of X-ray detectors;
generating a signal indicative of the detected X-rays; and
reconstructing the signal to generate image data indicative of the field of view;
wherein a width of each row of the plurality of rows is different and a function of a declination angle of a line from the focal spot to a corresponding row relative to the rotation axis.

16. The method according to claim 15 wherein the width of each row of X-ray detectors increases as the declination angle increases.

17. The method according to claim 15 wherein the width of each row of X-ray detectors is a function of $1/\sin(\beta+\phi)$, wherein $\phi$ is the declination angle of the row and $\beta$ is the angle at which the focal spot is tilted with respect to the rotation plane.

18. The method according to claim 15 wherein the width of each row of X-ray detectors is a function of $1/(L*\sin(\beta+\phi))$, wherein L is a dimension of the focal spot along the direction along which the focal spot is tilted, $\phi$ is the declination angle of the row and $\beta$ is the angle at which the focal spot is tilted with respect to the rotation plane.

19. The method according to claim 15 wherein declination angles on a first side of the rotation axis have a first maximum magnitude and declination angles on a second side of the rotation axis have a second maximum magnitude, and an angle of the first maximum magnitude is a function of the heel effect.

* * * * *